United States Patent [19]

Schweikert et al.

[11] Patent Number: 4,628,106
[45] Date of Patent: Dec. 9, 1986

[54] PROCESS FOR THE PREPARATION OF 2-HYDROXY-(9H)-CARBAZOLE

[75] Inventors: Otto E. Schweikert, Kelkheim; Walter Reimann, Hofheim am Taunus; Werner Wykypiel, Rodgau; Karl E. Mack, Wiesbaden, all of Fed. Rep. of Germany

[73] Assignee: Hoechst Aktiengesellschaft, Frankfurt am Main, Fed. Rep. of Germany

[21] Appl. No.: 713,485

[22] Filed: Mar. 19, 1985

[30] Foreign Application Priority Data

Mar. 21, 1984 [DE] Fed. Rep. of Germany ....... 3410232

[51] Int. Cl.$^4$ ............................................ C07D 209/88
[52] U.S. Cl. .................................... 548/440; 548/446
[58] Field of Search ................................ 548/440, 446

[56] References Cited

FOREIGN PATENT DOCUMENTS 778861  3/1935  France .

OTHER PUBLICATIONS

Cummins et al., *J. Chem. Soc.* (1955), pp. 3475–3477.

*Primary Examiner*—Robert W. Ramsuer
*Attorney, Agent, or Firm*—Curtis, Morris & Safford

[57] ABSTRACT

The invention relates to a process for the preparation of 2-hydroxy-(9H)-carbazole. In this process, 1,2,3,4-tetrahydro-7-hydroxy-(9H)-carbazole is dehydrogenated in an inert organic solvent.

1 Claim, No Drawings

PROCESS FOR THE PREPARATION OF 2-HYDROXY-(9H)-CARBAZOLE

The invention relates to a process for the preparation of 2-hydroxy-(9H)-carbazole (HC) by catalytic dehydrogenation of 1,2,3,4-tetrahydro-7-hydroxy-(9H)-carbazole (THC).

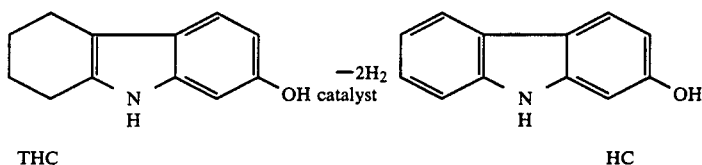

HC is an important intermediate for the preparation of dyestuffs; for this azylic acid (2-hydroxy-(9H)-carbazole-1-carboxylic acid) is in general first prepared from HC.

Processes for the preparation of HC are already known. According to U.S. Pat. No. 4,137,238, HC is prepared by cyclizing 2-chloro-3'-hydroxydiphenylamine with bases. The disadvantage here is that the reaction is carried out in dilute solutions (low space-time yields). In addition, salt-containing effluents are obtained as a result of the necessary neutralization of the reaction product.

The preparation of HC by catalytic dehydrogenation of THC is described in J. Chem. Soc. 1955, page 3475. THC is mixed with Pd/C and heated to 270° C. in a $CO_2$ atmosphere in the absence of a solvent. However, this process also has the disadvantage that the reaction product must be treated with sodium hydroxide solution, so that the Na salt of HC is initially formed, from which HC must be obtained by treatment with acid. The authors give no information on the yields.

The aim of the present invention is to provide a non-polluting process for the preparation of HC by dehydrogenation of the THC accessible in accordance with the literature (Chem. Ber. 92, 2385 (1959)).

The process for the preparation of 2-hydroxy-(9H)-carbazole by catalytic dehydrogenation of 1,2,3,4-tetrahydro-7-hydroxy-(9H)-carbazole comprises carrying out the reaction in an inert organic solvent.

It is an advantage of the novel process that HC can be isolated in a simple manner, without addition of further auxiliaries, from the reaction solution which has been freed from the catalyst. This is in general effected by a procedure in which the solvent is completely or partly evaporated off and HC crystallizes out. The solvent evaporated off and condensed is used again.

Examples of suitable inert solvents are aliphatic and aromatic ethers, such as di-iso-propyl ether, di-n-butyl ether, di-iso-amyl ether, dioctyl ether, dimethyldiglycol, diethyldiglycol, anisole and phenetole. Other solvents which are suitable are aliphatic and aromatic hydrocarbons, such as n-nonane, n-decane, cis- and trans-decalin, xylenes, mesitylene, n-butylbenzene, tetralin, 1,3-diisopropylbenzene and α- and β-methylnaphthalene. Preferred solvents of this type are ethers, in particular dimethyldiglycol and diethyldiglycol.

However, alcohols and ether-alcohols and mixtures thereof are even more advantageous. In particular, these solvents in general have a different dissolving power for the starting substance THC and the end product HC, so that highly pure HC can be isolated after cooling the reaction solution. If appropriate, the solvent is partly evaporated off before the cooling, or, if a solvent mixture is used, the solvent with the lower boiling point and the component which dissolves the THC well is evaporated off. At the same time, crystallization of HC out of the reaction solution enables THC of poorer purity to be used as the starting material. Examples of suitable alcohols and ether-alcohols are: amyl alcohol, cyclohexanol, 2-ethylhexanol, octanol, decanol, methylglycol, n-butylglycol and t-butylglycol.

Preferred solvents are: 2-ethylhexanol, octanol and n-butylglycol. The successful use of alcohols and ether-alcohols is surprising inasmuch as it is known from the literature that these compounds tend to split off CO and $H_2$ rapidly at elevated temperature in the presence of hydrogenation or dehydrogenation catalysts.

The reaction temperatures are in the range from 120° to 300° C., and are preferably 140°–220° C., in particular 170°–190° C. The reaction is in general carried out at the boiling point of the chosen solvent. In this case, the maximum reaction temperature is given by the boiling point of the solvent, which can also be increased by applying pressure. If desired, the boiling point of the solvent can also be reduced by applying reduced pressure.

Suitable catalysts are all the customary hydrogenation and dehydrogenation catalysts, such as palladium, ruthenium, rhodium, iridium, platinum and nickel, in finely divided form or on supports. Mixtures of these metals are also suitable for the reaction.

Examples of supports which can be used are: charcoal, $SiO_2$, $Al_2O_3$, aluminum silicates, spinels, chromium oxide/aluminum oxides and zeolites. The concentration of the metal on the support here is in general 0.1–15% by weight. When the reaction has ended, the catalyst is filtered off and can be used again.

The process according to the invention can be carried out continuously or batchwise.

The following examples are intended to illustrate the process according to the invention.

EXAMPLE 1

187 g of THC were dissolved in 1.5 l of dimethyldiglycol. After addition of 50 g of Pd/charcoal (10% by weight of Pd) as a catalyst, the apparatus was flushed with nitrogen and the mixture was then heated at 165° C. for 3 hours, with stirring. During this time, 42.5 l (S.T.P.) of hydrogen were evolved. After the reaction mixture had been cooled, the catalyst was filtered off and the filtrate was evaporated to dryness. The residue was ground in a mortar and dried in vacuo (70° C., 50 mbar) for 4 hours. 180.4 g of crude HC containing 96.4% by weight of HC, 2.3% by weight of dimethyldiglycol and still 1.3% by weight of unreacted THC were obtained. This corresponds to a yield of pure HC of 95%.

EXAMPLE 2

187 g of THC (degree of purity: 70%) were dissolved in 1.5 l of 2-ethylhexanol, with warming, 100 g of Pd/charcoal (5% by weight of Pd) were added and the mixture was covered with a layer of nitrogen. The mixture was heated at 185° C. for 3 hours, with stirring, 41 l (S.T.P.) of hydrogen being released. The catalyst was filtered off hot and washed out with 0.5 l of hot 2-ethylhexanol. The filtrate was evaporated to a volume of 750 ml and then cooled to room temperature. The HC which had crystallized out was filtered off with suction and dried in vacuo (70° C., 50 mbar). 111 g of HC (degree of purity: 98%) with a melting point of 276° C. were obtained. Yield: 85% of pure HC.

EXAMPLE 3

374 g of THC (degree of purity: 84%) were dissolved in a mixture of 1.5 l of 2-ethylhexanol and 0.5 l of n-butylglycol, 100 g of Pd/charcoal (5% by weight of Pd) were added and the mixture was covered with a layer of nitrogen. The mixture was heated at 180° C. for 4 hours, 71 l (S.T.P.) of hydrogen escaping. The catalyst was filtered off hot and washed out with 0.5 l of hot solvent mixture. The filtrate was evaporated to a volume of 1.5 l over a 50 cm packed column, the low-boiling n-butylglycol chiefly being distilled off. After the mixture had cooled to room temperature, the HC which had crystallized out was filtered off with suction and dried in vacuo (70° C., 50 mbar). 287 g of HC (degree of purity: 98.5%) were obtained. Yield: 92% of pure HC.

We claim:

1. A process for the preparation of 2-hydroxy-(9H)-carbazole, which comprises catalytically hydrogenating 1,2,3,4-tetrahydro-7-hydroxy-(9H)-carbazole in an inert organic solvent selected from the group consisting of alcohols, ether alcohols and mixtures thereof.

* * * * *

UNITED STATES PATENT AND TRADEMARK OFFICE
CERTIFICATE OF CORRECTION

PATENT NO. : 4,628,106
DATED      : December 9, 1986
INVENTOR(S) : Schweikert et al.

It is certified that error appears in the above-identified patent and that said Letters Patent is hereby corrected as shown below:

Column 4, line 15 change "hydrogenating" to --dehydrogenating--.

Signed and Sealed this

Twenty-fourth Day of March, 1987

Attest:

DONALD J. QUIGG

Attesting Officer

Commissioner of Patents and Trademarks